US009974542B2

(12) United States Patent
Hodgkinson

(10) Patent No.: US 9,974,542 B2
(45) Date of Patent: May 22, 2018

(54) SURGICAL APPARATUS INCLUDING SURGICAL BUTTRESS

(71) Applicant: Covidien LP, Mansfield, MA (US)

(72) Inventor: Gerald N. Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 78 days.

(21) Appl. No.: 15/255,455

(22) Filed: Sep. 2, 2016

(65) Prior Publication Data

US 2016/0367253 A1   Dec. 22, 2016

Related U.S. Application Data

(62) Division of application No. 13/747,525, filed on Jan. 23, 2013, now Pat. No. 9,433,420.

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/072* (2013.01);
(Continued)

(58) Field of Classification Search
CPC ............... A61B 17/068; A61B 17/072; A61B 17/07207; A61B 17/07292; A61B 17/115;
(Continued)

(56) References Cited

U.S. PATENT DOCUMENTS 3,054,406 A   9/1962 Usher
3,079,606 A   3/1963 Bobrov et al.
(Continued)

FOREIGN PATENT DOCUMENTS

CA   2282761 A1   9/1998
CA   2667434 A1   5/2008
(Continued)

OTHER PUBLICATIONS

Chinese First Office Action corresponding to counterpart Int'l Appln. No. CN 2013107068710 dated Dec. 16, 2016.
(Continued)

*Primary Examiner* — Scott A. Smith

(57) ABSTRACT

A surgical stapling apparatus includes a housing, an end effector, fasteners, and one or more surgical buttresses. The end effector is secured to the housing and has first and second jaw assemblies. The first jaw assembly defines slots and the second jaw assembly defines pockets. One or both of the first and second jaw assemblies define recesses. The fasteners are disposed in the slots of the first jaw assembly and are formed by the pockets of the second jaw assembly. The one or more surgical buttresses have a body that includes plugs that are integrally formed with the body for insertion into the recesses to secure the surgical buttress(es) to one or both of the first and second jaw assemblies. The body substantially overlies at least some of the slots of the first jaw assembly and/or at least some of the pockets of the second jaw assembly.

16 Claims, 3 Drawing Sheets

(51) Int. Cl.
    *B29C 65/02* (2006.01)
    *B29C 65/70* (2006.01)
    *A61B 17/00* (2006.01)
    *B29L 31/00* (2006.01)

(52) U.S. Cl.
    CPC ........ *A61B 17/07292* (2013.01); *B29C 65/02* (2013.01); *B29C 65/70* (2013.01); *A61B 2017/00526* (2013.01); *A61B 2017/07214* (2013.01); *B29K 2995/006* (2013.01); *B29L 2031/7546* (2013.01)

(58) Field of Classification Search
    CPC ...... A61B 17/1155; A61B 2017/07214; A61B 2017/00526
    USPC .............. 227/19, 175.1, 176.1, 175.2, 180.1; 606/139, 143, 151, 153, 219
    See application file for complete search history.

(56) References Cited

U.S. PATENT DOCUMENTS

| | | |
|---|---|---|
| 3,124,136 A | 3/1964 | Usher |
| 3,490,675 A | 1/1970 | Green et al. |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,112,496 A | 5/1992 | Dhawan et al. |
| 5,137,198 A | 8/1992 | Nobis et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,865,361 A | 2/1999 | Milliman et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,202,914 B1 | 3/2001 | Geiste et al. |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,568,398 B2 | 5/2003 | Cohen |
| 6,592,597 B2 | 7/2003 | Grant et al. |
| 6,610,006 B1 | 8/2003 | Amid et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |

(56) References Cited

U.S. PATENT DOCUMENTS

| | | |
|---|---|---|
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,983 B2 | 10/2011 | Chu et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,146,791 B2 | 4/2012 | Bettuchi et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,328,111 B2 | 5/2016 | Zhou et al. |
| 9,351,729 B2 | 5/2016 | Orban, III et al. |
| 9,358,005 B2 | 6/2016 | Shelton, IV et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Milliman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,844,378 B2 * | 12/2017 | Casasanta ............ A61B 17/105 |
| 2002/0028243 A1 | 3/2002 | Masters |
| 2002/0091397 A1 | 7/2002 | Chen |
| 2002/0165559 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0208231 A1 | 11/2003 | Williamson et al. |

(56) References Cited

U.S. PATENT DOCUMENTS

| | | |
|---|---|---|
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2006/0004407 A1 | 1/2006 | Hiles et al. |
| 2006/0025816 A1 | 2/2006 | Shelton |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0215132 A1 | 9/2011 | Aranyi et al. |
| 2011/0215133 A1 | 9/2011 | Aranyi |
| 2011/0278346 A1 | 11/2011 | Hull et al. |
| 2011/0278347 A1 | 11/2011 | Olson et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0187179 A1 | 7/2012 | Gleiman |
| 2012/0197272 A1 | 8/2012 | Oray et al. |
| 2012/0241499 A1 | 9/2012 | Baxter, III et al. |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |

(56) References Cited

U.S. PATENT DOCUMENTS

| | | |
|---|---|---|
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |

FOREIGN PATENT DOCUMENTS

| | | |
|---|---|---|
| CN | 1383788 A | 12/2002 |
| CN | 101310680 A | 11/2008 |
| CN | 101332110 A | 12/2008 |
| CN | 101507639 A | 8/2009 |
| DE | 1602563 U | 3/1950 |
| DE | 19924311 A1 | 11/2000 |
| EP | 0327022 A2 | 8/1989 |
| EP | 0594148 A1 | 4/1994 |
| EP | 0667119 A1 | 8/1995 |
| EP | 1064883 A1 | 1/2001 |
| EP | 1256317 A2 | 11/2002 |
| EP | 1256318 A1 | 11/2002 |
| EP | 1520525 A1 | 4/2005 |
| EP | 1621141 A2 | 2/2006 |
| EP | 1702570 A1 | 9/2006 |
| EP | 1759640 A2 | 3/2007 |
| EP | 1815804 A2 | 8/2007 |
| EP | 1825820 A1 | 8/2007 |
| EP | 1929958 A2 | 6/2008 |
| EP | 1994890 A1 | 11/2008 |
| EP | 2005894 A2 | 12/2008 |
| EP | 2005895 A2 | 12/2008 |
| EP | 2008595 A2 | 12/2008 |
| EP | 2039302 A2 | 3/2009 |
| EP | 2039308 A2 | 3/2009 |
| EP | 2090231 A1 | 8/2009 |
| EP | 2090244 A2 | 8/2009 |
| EP | 2090252 A2 | 8/2009 |
| EP | 2163211 A2 | 3/2010 |
| EP | 2189121 A1 | 5/2010 |
| EP | 2198787 A1 | 6/2010 |
| EP | 2236098 A2 | 10/2010 |
| EP | 2236099 A1 | 10/2010 |
| EP | 2258282 A2 | 12/2010 |
| EP | 2292276 A2 | 3/2011 |
| EP | 2311386 A2 | 4/2011 |
| EP | 2436348 A1 | 4/2012 |
| EP | 2462880 A2 | 6/2012 |
| EP | 2497431 A1 | 9/2012 |
| EP | 2517637 A1 | 10/2012 |
| EP | 2586380 A1 | 5/2013 |
| EP | 2604195 A1 | 6/2013 |
| EP | 2604197 A2 | 6/2013 |
| EP | 2620105 A1 | 7/2013 |
| EP | 2620106 A2 | 7/2013 |
| EP | 2630922 A1 | 8/2013 |
| EP | 2644125 A2 | 10/2013 |
| EP | 2762091 A2 | 8/2014 |
| JP | 2000166933 A | 6/2000 |
| JP | 2001286477 A | 10/2001 |
| JP | 2002202213 A | 7/2002 |
| JP | 2002-369820 A | 12/2002 |
| JP | 2007-505708 A | 3/2007 |
| JP | 2007124166 A | 5/2007 |
| JP | 2009189846 A | 8/2009 |
| JP | 2011078763 A | 4/2011 |
| WO | 9005489 A1 | 5/1990 |
| WO | 9516221 A1 | 6/1995 |
| WO | 9622055 A1 | 7/1996 |
| WO | 9701989 A1 | 1/1997 |
| WO | 9713463 A1 | 4/1997 |
| WO | 9817180 A1 | 4/1998 |
| WO | 9945849 A1 | 9/1999 |
| WO | 03082126 A1 | 10/2003 |
| WO | 03088845 A2 | 10/2003 |
| WO | 03094743 A1 | 11/2003 |
| WO | 03105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. CN 2013103036903 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
Japanese Office Action corresponding to Japanese Patent Application No. 2014-009738 dated Nov. 14, 2017.
European Office Action corresponding to counterpart Int'l Appln. No. EP 14 17 2681.0 dated May 13, 2016.

(56) References Cited

OTHER PUBLICATIONS

Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Extended European Search Report corresponding to EP 13 17 7437.4, completed Sep. 11, 2013 and dated Sep. 19, 2013; (6 pp).
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
Extended European Search Report corresponding to EP No. 12 19 1035.0, completed Jan. 11, 2013 and dated Jan. 18, 2013; 7 pages.
Extended European Search Report corresponding to EP No. 12 18 6175.1, completed Jan. 15, 2013 and dated Jan. 23, 2013; 7 pages.
Extended European Search Report corresponding to EP No. 12 19 1114.3, completed Jan. 23, 2013 and dated Jan. 31, 2013; 10 pages.
Extended European Search Report corresponding to EP No. 12 19 2224.9, completed Mar. 14, 2013 and dated Mar. 26, 2013; 8 pages.
Extended European Search Report corresponding to EP No. 12 19 6911.7, completed Apr. 18, 2013 and dated Apr. 24, 2013; 8 pages.
Extended European Search Report corresponding to EP 08 72 6500.5, completed Feb. 20, 2014 and dated Mar. 3, 2014; (7 pp).
Extended European Search Report corresponding to EP 13 19 5919.9, completed Feb. 10, 2014 and dated Mar. 3, 2014; (7 pp).
Extended European Search Report corresponding to EP 13 19 2123.1, completed Jan. 30, 2014 and dated Feb. 10, 2014; (8 pp).
Extended European Search Report corresponding to EP 13 19 6816.6, completed Mar. 28, 2014 and dated Apr. 9, 2014; (9 pp).
Extended European Search Report corresponding to EP 13 19 4995.0, completed Jun. 5, 2014 and dated Jun. 16, 2014; (5 pp).
Extended European Search Report corresponding to EP 13 19 5019.8, completed Mar. 14, 2014 and dated Mar. 24, 2014; (7 pp).
Extended European Search Report corresponding to EP 13 19 2111.6, completed Feb. 13, 2014 and dated Feb. 27, 2014; (10 pp).
Extended European Search Report corresponding to EP 13 19 7958.5, completed Apr. 4, 2014 and dated Apr. 15, 2014; (8 pp).
Extended European Search Report corresponding to EP 14 15 6342.9, completed Jul. 22, 2014 and dated Jul. 29, 2014; (8 pp).
Extended European Search Report corresponding to EP 14 15 7195.0, completed Jun. 5, 2014 and dated Jun. 18, 2014; (9 pp).
Extended European Search Report corresponding to EP 12 19 1035.0, completed Jan. 11, 2013 and dated Jan. 18, 2013; 7 pages.
Extended European Search Report corresponding to EP 12 19 6904.2, completed Mar. 28, 2013 and dated Jul. 26, 2013; 8 pages.
Extended European Search Report corresponding to EP 12 19 8749.9, completed May 21, 2013 and dated May 31, 2013; 8 pages.
Extended European Search Report corresponding to EP 07 00 5842.5, completed May 13, 2013 and dated May 29, 2013; 7 pages.
Extended European Search Report corresponding to EP 12 19 8776.2, completed May 16, 2013 and dated May 27, 2013; 8 pages.
Extended European Search Report corresponding to EP 13 15 6297.7, completed Jun. 4, 2013 and dated Jun. 13, 2013; 7 pages.
Extended European Search Report corresponding to EP 13 17 3985.6, completed Aug. 19, 2013 and dated Aug. 28, 2013; 6 pages.
Extended European Search Report corresponding to EP 13 17 3986.4, completed Aug. 20, 2013 and dated Aug. 29, 2013; 7 pages.
International Search Report corresponding to European Application No. EP 05 02 2585.3, completed on Jan. 25, 2006 and dated Feb. 3, 2006; 4 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and dated Jan. 11, 2007; 10 pages.
International Search Report corresponding to International Application No. PCT/US05/36740, completed on Feb. 20, 2007 and dated Mar. 23, 2007; 8 pages.
International Search Report corresponding to International Application No. PCT/US2007/022713, completed on Apr. 21, 2008 and dated May 15, 2008; 1 page.
International Search Report corresponding to International Application No. PCT/US2008/002981, completed on Jun. 9, 2008 and dated Jun. 26, 2008; 2 pages.

(56) References Cited

OTHER PUBLICATIONS

International Search Report corresponding to European Application No. EP 08 25 1779, completed on Jul. 14, 2008 and dated Jul. 23, 2008; 5 pages.
International Search Report corresponding to European Application No. EP 08 25 1989.3, completed on Mar. 11, 2010 and dated Mar. 24, 2010; 6 pages.
Chinese Office Action dated Mar. 2, 2017 in corresponding Chinese Patent Application No. 201410028462.4 together with English translation, 27 pages.
European Office Action dated Mar. 7, 2017 in corresponding European Patent Application No. 14152060.1, 4 pages.
Australian Examination Report for application No. 2013273613 dated Jun. 28, 2017.
International Search Report corresponding to European Application No. EP 10 25 0639.1, completed on Jun. 17, 2010 and dated Jun. 28, 2010; 7 pages.
International Search Report corresponding to European Application No. EP 10 25 0715.9, completed on Jun. 30, 2010 and dated Jul. 20, 2010; 3 pages.
International Search Report corresponding to European Application No. EP 05 80 4382.9, completed on Oct. 5, 2010 and dated Oct. 12, 2010; 3 pages.
International Search Report corresponding to European Application No. EP 10 25 1437.9, completed on Nov. 22, 2010 and dated Dec. 16, 2010; 3 pages.
International Search Report corresponding to European Application No. EP 09 25 2897.5, completed on Feb. 7, 2011 and dated Feb. 15, 2011; 3 pages.
International Search Report corresponding to European Application No. EP 10 25 0642.5, completed on Mar. 25, 2011 and dated Apr. 4, 2011; 4 pages.
International Search Report corresponding to European Application No. EP 11 18 8309.6, completed on Dec. 15, 2011 and dated Jan. 12, 2012; 3 pages.
International Search Report corresponding to European Application No. EP 12 15 2229.6, completed on Feb. 23, 2012 and dated Mar. 1, 2012; 4 pages.
International Search Report corresponding to European Application No. EP 12 15 0511.9, completed on Apr. 16, 2012 and dated Apr. 24, 2012; 7 pages.
International Search Report corresponding to European Application No. EP 12 15 2541.4, completed on Apr. 23, 2012 and dated May 3, 2012; 10 pages.
International Search Report corresponding to European Application No. EP 12 16 5609.4, completed on Jul. 5, 2012 and dated Jul. 13, 2012; 8 pages.
International Search Report corresponding to European Application No. EP 12 15 8861.0, completed on Jul. 17, 2012 and dated Jul. 24, 2012; 9 pages.
International Search Report corresponding to European Application No. EP 12 16 5878.5, completed on Jul. 24, 2012 and dated Aug. 6, 2012; 8 pages.
Extended European Search Report corresponding to EP 14152060.0 dated Aug. 14, 2015.
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Chinese Office Action corresponding to counterpart Int'l Appln No. CN 201210129787.2 dated Aug. 24, 2015.
European Office Action dated Aug. 4, 2016 in European Patent Application No. 14152060, 5 pages.

\* cited by examiner

SURGICAL APPARATUS INCLUDING SURGICAL BUTTRESS

CROSS-REFERENCE TO RELATED APPLICATIONS

This application is a divisional and claims the benefit of and priority to U.S. patent application Ser. No. 13/747,525, filed Jan. 23, 2013, now U.S. Pat. No. 9,433,420, the entire disclosure of which is incorporated by reference herein.

BACKGROUND

Technical Field

This application relates to a surgical apparatus, and more particularly, to a surgical buttress for use with a surgical stapling apparatus during operation of the stapling apparatus to apply a plurality of surgical staples to body tissue.

Background of Related Art

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

Although the present disclosure includes, but is not limited to use with endoscopic surgery, endoscopic surgery is one of the truly great advances in recent years to reduce the invasiveness of surgical procedures. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

In many surgical procedures, including those involved in open and endoscopic surgery, it is often necessary to staple tissue. It is especially challenging during endoscopic surgery because of the small openings through which the stapling of tissues must be accomplished. Instruments for this purpose can include two elongated members which are respectively used to capture or clamp tissue. Surgical devices wherein tissue is first grasped or clamped between opposing jaw structure and then joined by surgical fasteners are well known in the art. Typically, one of the members carries a fastener cartridge which houses a plurality of staples arranged in at least two lateral rows while the other member has an anvil that defines a surface for forming the staple legs as the staples are driven from the staple cartridge. The fasteners are typically in the form of surgical staples but two part polymeric fasteners can also be utilized. Generally, the stapling operation is effected by cam bars or wedges that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapling apparatus disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. U.S. Surgical, the assignee of the present application, has manufactured and marketed endoscopic stapling instruments for several years. Examples of such instruments include the Multifire ENDO GIA™ 30 and Multifire ENDO GIA™ 60 instruments. Other examples of such stapling apparatuses are disclosed in U.S. Pat. Nos. 4,429,695 and 5,065,929.

In stapling apparatuses of the general type described above, surgical buttress material may be used in combination with these instruments as reinforcement to staple lines to further promote proper staple formation while reducing twisting/malformation caused by any misalignment or unusual or non-uniform tissue. These instruments have provided significant clinical benefits. Nonetheless, improvements are possible, for example, by reducing the complexity of manufacture and/or application.

SUMMARY

According to one aspect, the present disclosure relates to a surgical stapling apparatus including a housing, an end effector, a plurality of fasteners, and one or more surgical buttresses.

The end effector is secured to the housing and has first and second jaw assemblies. The first jaw assembly defines a plurality of fastener retaining slots. The second jaw assembly defines a plurality of fastener forming pockets. One or both of the first and second jaw assemblies defines a plurality of recesses formed in a tissue contacting surface thereof.

The plurality of fasteners is disposed in the fastener retaining slots of the first jaw assembly and configured and dimensioned to be formed by the fastener forming pockets of the second jaw assembly.

The one or more surgical buttresses have a body including a plurality of plugs extending therefrom. The plugs are integrally formed with the body and relatively positioned on the body for insertion into the plurality of recesses to secure the one or more surgical buttresses to one or both of the first jaw assembly and the second jaw assembly. The plurality of plugs is one of overmolded and deposited onto the one or more surgical buttresses at predetermined locations on the one or more surgical buttresses. The predetermined locations correspond to the locations of the plurality of recesses. The plurality of plugs may be made from a material selected from the group comprising polyglytone 6211, glycolide, caprolactone, trimethylene carbonate, lactide and combinations thereof. The body of the one or more surgical buttresses is configured and dimensioned to substantially overlie one or both of at least some of the fastener retaining slots of the first jaw assembly and at least some of the fastener forming pockets of the second jaw assembly. The one or more surgical buttresses may be formed of a non-woven material.

The first jaw assembly supports a cartridge defining the fastener forming slots. The one or more surgical buttresses are supported on a tissue contacting surface of the cartridge. The cartridge supports one or more pushers therein. Each of the plurality of plugs is configured and dimensioned such that when the plurality of plugs is positioned within the plurality of recesses, displacement of the one or more pushers results in displacement of one or more of the plurality of plugs from within one or more recesses of the plurality of recesses to facilitate the release of the one or more surgical buttresses from the cartridge upon a firing of the stapling apparatus.

One or more of the plurality of plugs is formed of a degradable polymer capable of mechanically interlocking within one or more of the plurality of recesses when exposed to heat and pressure to secure the one or more surgical buttresses to one or both of the first and second jaw assemblies. The plurality of plugs may be formed of a first material and the one or more surgical buttresses may be formed of a second material. The first material has a melting temperature below that of the second material. In particular, the first material may have a melting temperature of between about 120 degrees Celsius and about 150 degrees Celsius and the second material may have a melting temperature of between about 180 degrees Celsius to about 225 degrees Celsius.

The housing may support a knife assembly including a knife blade that is movable through one or both of the first and second jaw assemblies. The knife assembly may include a knife bar wherein the knife blade is secured to a distal end of the knife bar. The knife bar includes a top portion. The second jaw assembly includes an interior passage through which the top portion of the knife bar travels as the knife blade travels through a knife channel defined in the second jaw assembly. A portion of each of the plugs of the plurality of plugs extends into the interior passage of the second jaw assembly to facilitate the securement of the one or more surgical buttresses to the second jaw assembly. The top portion of the knife bar mechanically disrupts the portion of each of the plugs that extends into the interior passage of the second jaw assembly to facilitate a release of the one or more surgical buttresses from the second jaw assembly as the top portion of the knife bar travels through the interior passage of the second jaw assembly.

The first and second jaw assemblies may be circular and the second jaw assembly may support a cut ring. The plurality of plugs of the one or more surgical buttress are secured to the cut ring at a location radially inward of an annular knife blade such that contact of the annular knife blade against the cut ring severs the one or more surgical buttresses to release a portion of the one or more surgical buttresses located radially outward of the annular knife blade from the second jaw assembly after a firing of the stapling apparatus.

According to another aspect, an end effector for a surgical stapling apparatus includes a first jaw assembly, a second jaw assembly, a plurality of fasteners, and one or more surgical buttresses.

The first jaw assembly defines a plurality of fastener retaining slots and the second jaw assembly defines a plurality of fastener forming pockets. The plurality of fasteners is disposed in the fastener retaining slots of the first jaw assembly and configured and dimensioned to be formed by the fastener forming pockets of the second jaw assembly. One or both of the first and second jaw assemblies define a plurality of recesses.

The one or more surgical buttresses have a body including a plurality of plugs extending therefrom. The body is configured and dimensioned to substantially overlie one or both of at least some of the fastener retaining slots of the first jaw assembly and at least some of the fastener forming pockets of the second jaw assembly. The plugs are integrally formed with the body and positioned within the plurality of recesses to secure the one or more surgical buttress to one or both of the first jaw assembly and the second jaw assembly. The plurality of plugs may be made from a material selected from the group comprising polyglytone 6211, glycolide, caprolactone, trimethylene carbonate, lactide and combinations thereof. The plurality of plugs may be one of overmolded and deposited onto the one or more surgical buttresses at predetermined locations on the one or more surgical buttresses. The predetermined locations correspond to the locations of the plurality of recesses on one or more of the first and second jaw assemblies.

The first jaw assembly supports a cartridge defining the fastener forming slots. The one or more surgical buttresses are supported on a tissue contacting surface of the cartridge. The cartridge supports one or more pushers therein. Each of the plurality of plugs is configured and dimensioned such that when the plurality of plugs is positioned within the plurality of recesses, displacement of the one or more pushers results in displacement of one or more of the plurality of plugs from within one or more recesses of the plurality of recesses to facilitate the release of the one or more surgical buttresses from the cartridge upon a firing of the stapling apparatus.

One or more of the plurality of plugs may be formed of a degradable polymer capable of mechanically interlocking within one or more of the plurality of recesses when exposed to heat and pressure to secure the one or more surgical buttress to one or both of the first and second jaw assemblies. The plurality of plugs may be formed of a first material and the one or more surgical buttresses may be formed of a second material. The first material has a melting temperature below that of the second material. The first material may have a melting temperature of between about 120 degrees Celsius and about 150 degrees Celsius and the second material may have a melting temperature of between about 180 degrees Celsius to about 225 degrees Celsius.

According to one aspect, a method of mounting a surgical buttress to an end effector for a surgical stapling apparatus includes providing an end effector for a surgical stapling apparatus. The end effector includes a first jaw assembly defining a plurality of fastener retaining slots and a second jaw assembly defining a plurality of fastener forming pockets. One or both of the first and second jaw assemblies define a plurality of recesses. The method involves providing a surgical buttress formed of a first material, providing a second material on the surgical buttress at predetermined locations on the surgical buttress, placing the surgical buttress against a tissue contacting surface of one of the first jaw assembly and the second jaw assembly, exposing the surgical buttress to heat and pressure to move the second material into the plurality of recesses, and removing the heat and pressure to interlock the second material within the plurality of recesses to secure the surgical buttress on one or both of the first jaw assembly and the second jaw assembly. The step of exposing the surgical buttress to heat and pressure may result in a forming of the second material into a plurality of plugs integrally extending from the surgical buttress and that interlock within the plurality of recesses to secure the surgical buttress on one or both of the first jaw assembly and the second jaw assembly.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Figure 1:
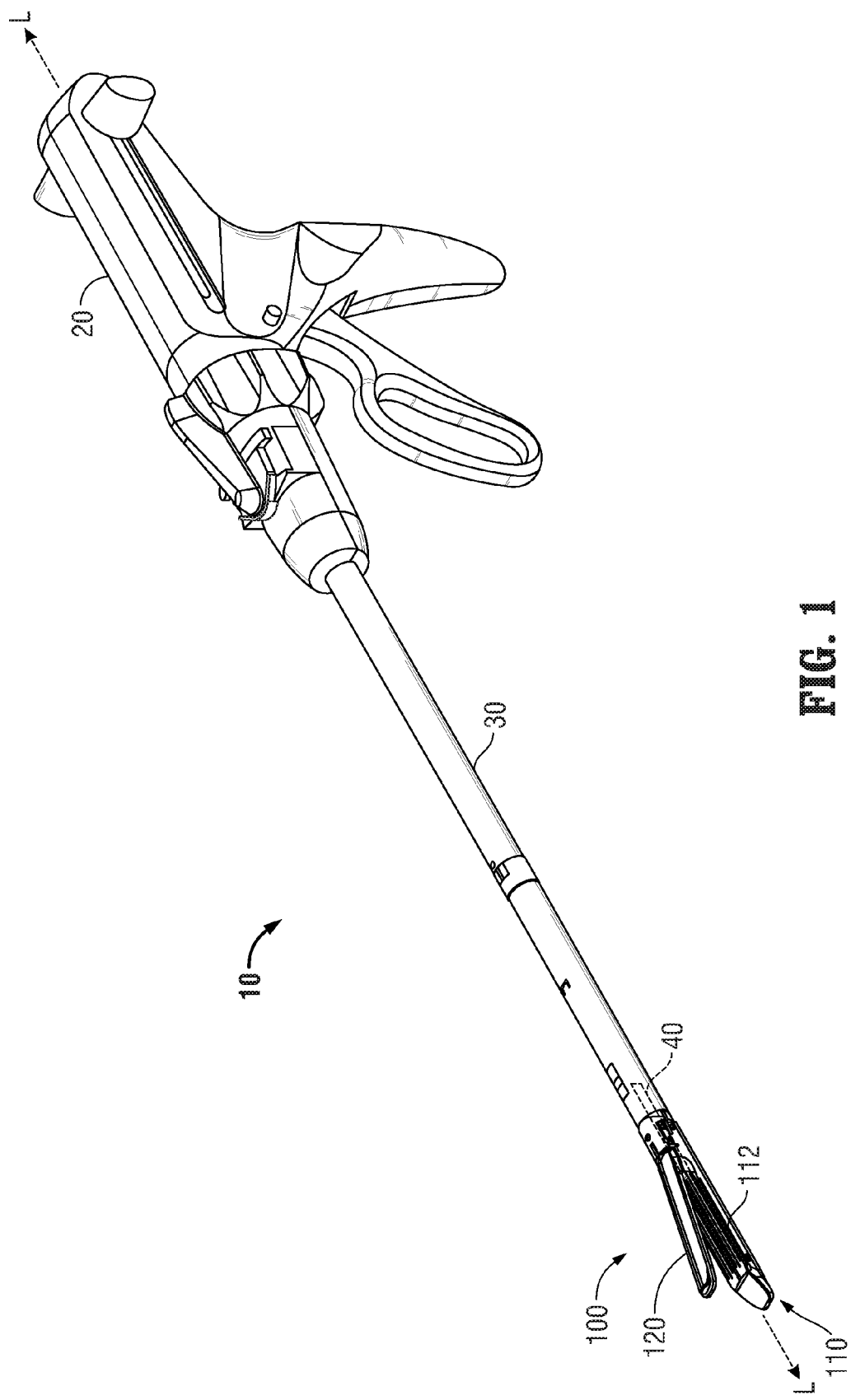
FIG. 1 is a perspective view of an endoscopic surgical stapling apparatus in accordance with the present disclosure.

As used herein, the term "clinician" refers to a doctor, a nurse, or any other care provider and may include support personnel. Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the clinician and the term "distal" refers to the end of the apparatus that is farther from the clinician. In the following description, well-known functions or constructions are not described in detail to avoid obscuring the present disclosure in unnecessary detail.

In general, linear stapling apparatuses, including open and endoscopic devices, can have two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such an instrument is disclosed, for example, in U.S. Pat. No. 6,202,914, the entire content of which is incorporated herein by reference.

Some stapling apparatuses apply a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. An example of such a stapling apparatus is disclosed in U.S. Pat. No. 5,065,929, the entire content of which is incorporated herein by reference.

Some of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,865,361, the entire content of which is incorporated herein by reference.

Referring now to the drawings, in which like reference numerals identify identical or substantially similar parts throughout the several views, FIG. 1 illustrates a surgical stapling apparatus 10 in accordance with the present disclosure that may be arranged for use with minimally invasive or open stapling procedures. The surgical stapling apparatus 10 includes a housing 20 and an elongate member 30 that extends distally from the housing 20. A distal end of the elongate member 30 supports a proximal end of an end effector 100. The end effector 100 defines a longitudinal axis "L" between the proximal and distal ends of the end effector 100 and includes a first jaw member and/or cartridge assembly 110 that is configured to selectively receive a staple cartridge 112 and a second jaw member and/or anvil assembly 120. The cartridge assembly 110 and the anvil assembly 120 are pivotably coupled at proximal ends thereof and may each support a surgical buttress 130, 230 (see FIGS. 2B and 3B) (as used herein, "surgical buttress" includes a pledget, gasket, buttress, or staple line reinforcement structure). The staple cartridge 112 houses staples and/or other surgical fasteners other than staples. The cartridge assembly 110 and the staple cartridge 112 may be selectively replaceable, either individually or collectively.

Figure 2A:
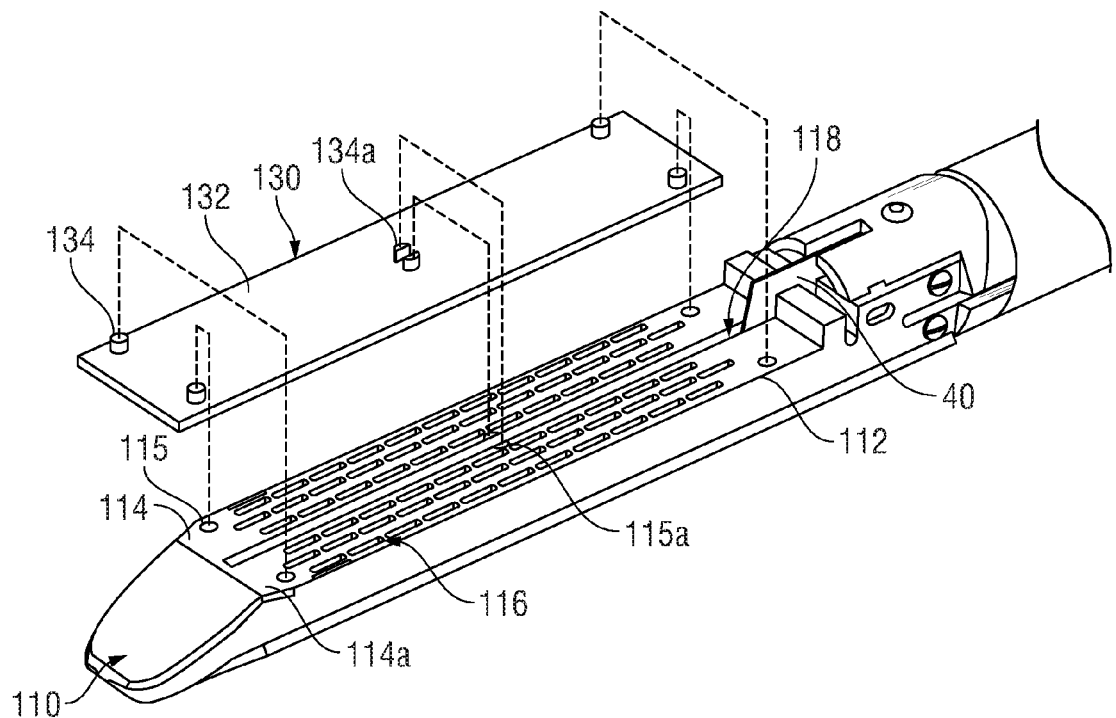
FIG. 2A is an enlarged perspective view illustrating a surgical buttress being secured to a cartridge assembly of the presently disclosed endoscopic surgical stapling apparatus.
Figure 2B:
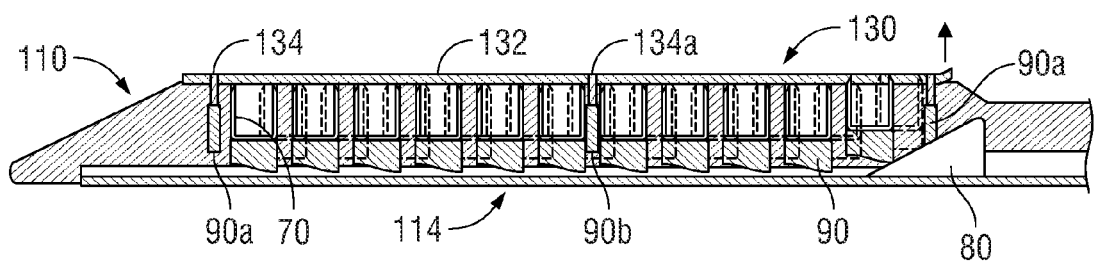
FIG. 2B is a cross-sectional view of the cartridge assembly and the surgical buttress shown in FIG. 2A with the surgical buttress being shown secured to the cartridge assembly.
Figure 2C:
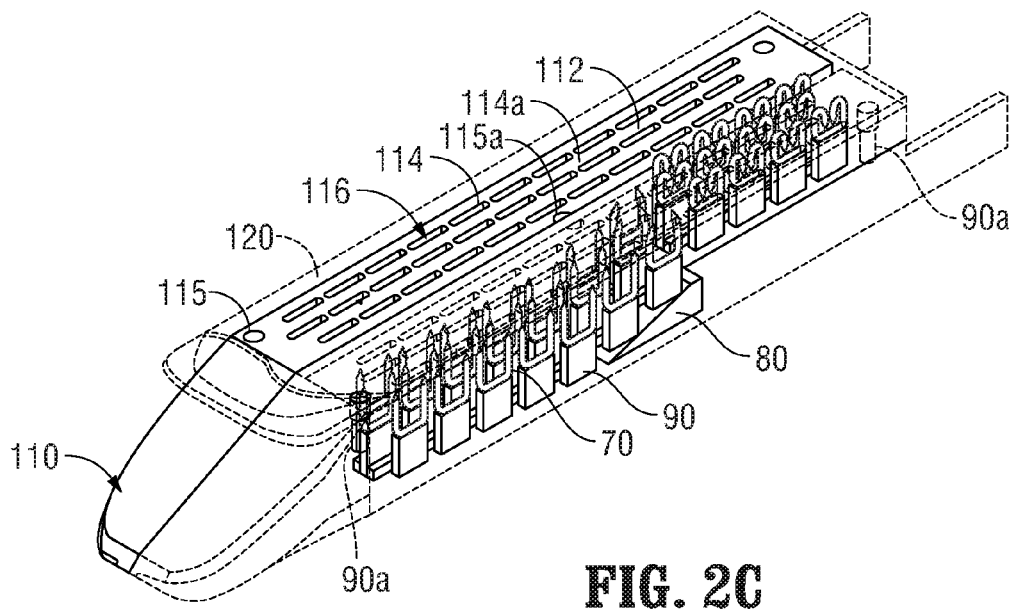
FIG. 2C is an enlarged perspective view illustrating an end effector of the presently disclosed surgical stapling apparatus during a fastener applying operation as fasteners are being sequentially fired.
Figure 3A:
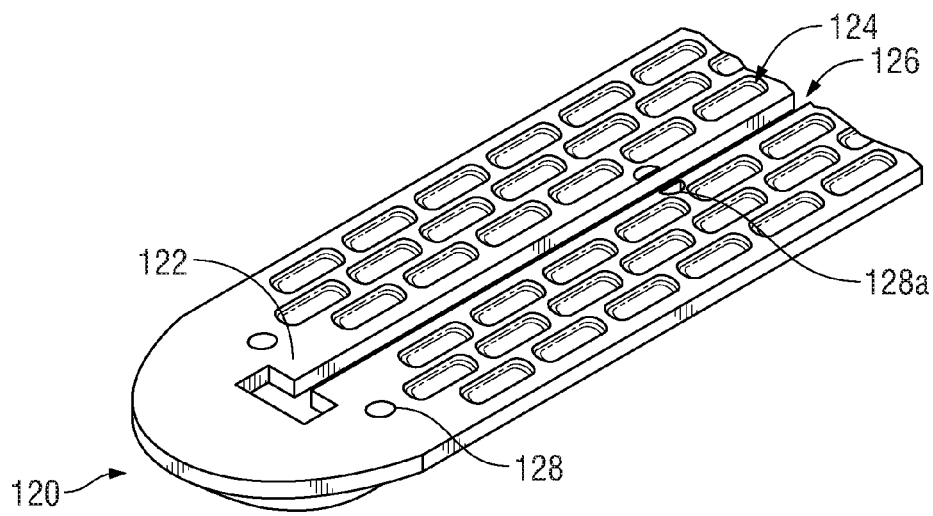
FIG. 3A is a bottom perspective view of an anvil assembly of the end effector illustrated in FIG. 2C.

With reference to FIGS. 2A-2C, the staple cartridge 112 of the cartridge assembly 110 includes a cartridge housing 114 including a tissue contacting surface 114a having a plurality of rows of fastener retaining slots (also referred to herein as stapling apparatus slots and fastener slots) 116 formed therein that house a plurality of fasteners or staples 70. The staple cartridge 112 defines a cartridge knife channel 118 between proximal and distal ends of the staple cartridge 112 that is configured to receive a knife 40 (FIGS. 1 and 2A) that translates distally through the cartridge knife channel 118 to cut tissue clamped between the cartridge assembly 110 and the anvil assembly 120. Also with reference to FIG. 3A, the plurality of staples 70 may be sequentially formed in fastener forming pockets 124 defined in a tissue contacting surface of an anvil plate 122 of the anvil assembly 120, upon a distal advancement of a cam bar and/or a sled 80 supported in the cartridge housing 114, into a plurality of pusher members 90 supported in the cartridge housing 114. One or more pusher members 90a, 90b may also be supported in the cartridge housing 114. The anvil assembly 120 defines an anvil knife channel 126 between proximal and distal ends there and which is configured to receive the knife 40 as the knife 40 translates distally through the cartridge knife slot 118.

The tissue contacting surface 114a of the cartridge housing 114 defines one or more recesses therein that are configured to receive a portion of the surgical buttress 130 therein to secure the surgical buttress 130 to the cartridge assembly 110 as will be discussed in greater detail below. As shown in FIG. 2A, a recess 115 may be disposed at any suitable location along the tissue contacting surface 114a of the cartridge housing 114. For example, a plurality of recesses 115 may be disposed around the perimeter of the cartridge housing 114. Additionally or alternatively, a recess or a plurality of recesses 115a may be centrally disposed on the cartridge housing 114, for instance, adjacent to the knife channel 118. As appreciated, any of the recesses 115, 115a may have any suitable shape including circular, oval, polygonal, and combinations thereof.

Referring again to FIG. 3A, the tissue contacting surface 122 of the anvil assembly 120 defines one or more recesses therein that are configured to receive a portion of a surgical buttress 230 therein to secure the surgical buttress 230 to the anvil assembly 120 as will be discussed in greater detail below. A recess 128 may be disposed at any suitable location along the tissue contacting surface of the anvil plate 122 of the anvil assembly 120. For example, a plurality of recesses 128 may be disposed around the perimeter of the tissue contacting surface of the anvil plate 122 of the anvil assembly 120. Additionally or alternatively, a recess or a plurality of recesses 128a may be centrally disposed on the anvil plate 122 of anvil assembly 120, for instance, adjacent to the knife channel 126. As appreciated, any of the recesses 128, 128a may have any suitable shape including circular, oval, polygonal, and combinations thereof.

Figure 3B:
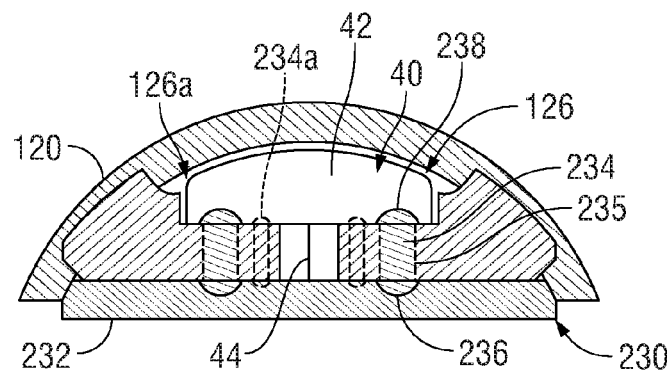
FIG. 3B is a cross-sectional view of the anvil assembly and a surgical buttress of the presently disclosed endoscopic surgical stapling apparatus with a knife of the presently disclosed endoscopic surgical stapling apparatus being shown translating through the anvil assembly and buttress upon the firing of the endoscopic surgical stapling apparatus.

Referring again to FIGS. 2A and 2B, the surgical buttress 130, which may be porous, non-porous, woven, and/or non-woven, includes a buttress body 132 and one or more plugs 134, 134a that extend from the buttress body 132 opposite a tissue contacting surface of the buttress body 132. Similarly, as shown in FIG. 3B, the surgical buttress 230, which may be porous, non-porous, woven, and/or non-woven, includes a buttress body 232 and one or more plugs 234 that extend from the buttress body 232 opposite a tissue contacting surface of the buttress body 232. The buttress bodies 132, 232, which may have a substantially rectangular shape, are configured to be secured to one or both of the cartridge assembly 110 and the anvil assembly 120 to provide fastener-line reinforcement for the plurality of staples 70 following the firing of the surgical stapling apparatus 10.

When the surgical buttress 130 is secured to the cartridge assembly 110 as shown in FIGS. 2A-2B, the buttress body 132 of the surgical buttress 130 overlies one or more of the fastener slots 116 of the tissue contacting surface 114a of the staple cartridge 112 such that a plug 134, 134a is supported within a recess 115, 115a of the staple cartridge 112 to maintain the buttress body 132 supported adjacent to/against the tissue contacting surface 114a of the staple cartridge 112.

Correspondingly, when the surgical buttress 230 is secured to anvil plate 122 of the anvil assembly 120 as shown in FIG. 3B, the buttress body 232 of the surgical buttress 230 overlies one or more of the fastener forming pockets 124 of the tissue contacting surface of the anvil plate 122 of the anvil assembly 120 such that a plug 234, 234a is supported within a recess 128, 128a of the anvil assembly 120 to maintain the buttress body 232 supported adjacent to/against the tissue contacting surface of the anvil plate 122 of the anvil assembly 120.

Of course, the surgical buttresses 130, 230 may be secured to the cartridge assembly and the anvil assembly by any suitable chemical and/or mechanical connection (e.g., adhesive, snap-fit, hook and loop type (Velcro®, Velcro Industries B.V. LTD LIAB CO NETHERLANDS) fasteners, straps, threads, etc.).

In embodiments, at least a portion of the surgical buttress 130, 230 may be made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, at least a portion of the surgical buttress 130, 230 may be made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes. In embodiments, the surgical buttresses 130, 230 or portions thereof, may be a non-woven material selected from the group including polyglytone 6211, glycolide, caprolactone, trimethylene carbonate, lactide and combinations thereof.

To attach one of the buttresses 130, 230 to the anvil assembly 120 or to the cartridge assembly 10, a bonding degradable polymer maybe overmolded or deposited onto the buttress body 132, 232, which is porous, at one or more predetermined locations. Next, heat and pressure are applied to the buttress 130, 230 to generate melt flow conditions. Then, under the melt flow conditions, a portion of the degradable polymer at each predetermined location is passed into a recess 115, 115a, 128, 128a while a portion of the degradable polymer is simultaneously passed into pores defined in the buttress body 132, 232. The degradable polymer is then solidified to mechanically interlock within the respective lateral recess 115, 115a, 128, 128a and within the pores of the buttress body 132, 232. In particular, the degradable polymer solidifies into a plug 134, 134a, 234, 234a to secure to the buttress body 132, 232 to one or both of the anvil assembly 120 and the cartridge assembly 110 adjacent to/against the tissue contacting surfaces of the respective anvil assembly 120 and cartridge assembly 110.

For example, as shown in FIG. 3B, each plug 234, 234a includes a body 235, a securement cap 238, and a securement base 236. Upon solidification of the plugs 234, 234a, the securement base 236 integrates the plugs 234, 234a within the buttress body 232 of the buttress 230 and the securement cap 238 facilitates securement of the plug body 235 within the respective recess 128, 128a. Notably, the securement cap 238 may project into the knife base portion 126a of the knife channel 126 defined within the anvil assembly 120, and abut against an inner surface of the anvil plate 122 of the anvil assembly 120, that defines the knife base portion 126a of the knife channel 126, to provide increased securement for supporting the buttress body 232 against the tissue contacting surface of the anvil plate 122 of the anvil assembly 120.

The degradable polymer of plugs 234, 234a may have a melting temperature below that of buttress body 132, 232 so that the degradable polymer can be melted without disrupting the physical properties of the buttress body 132, 232. In embodiments, the degradable polymer may include Caprosyn material which is an absorbable synthetic material prepared from POLYGLYTONE 6211, which includes glycolide, caprolactone, trimethylene carbonate, and Lactide. Caprosyn material has a melt temperature range of 125-145 degrees Celsius. The buttress body 132, 232 may include a synthetic material prepared from gylcolide (65 percent) and trimethylne carbonate (35 percent) in a 10 gallon Helcone reactor. In embodiments, the buttress body 132, 232 may include Maxon material which is a synthetic material prepared from polyglyconate, a copolymer of glycolic acid and trimethylene carbonate. The material of the buttress body 132, 232 may have a melting temperature between 185 degrees Celsius and 220 degrees Celsius. In embodiments, the buttress body 132, 232 may have a melting temperature between 210 degrees Celsius and 220 degrees Celsius and/or between 185 degrees Celsius and 200 degrees Celsius.

During operation of the surgical stapling apparatus 10, the cartridge assembly 110 and the anvil assembly 120 are clamped against tissue of a patient. As illustrated in FIGS. 2B-2C, the surgical stapling apparatus 10 is fired to deploy the fasteners 70 from the fastener slots 116. Upon firing, the sled 80 translates distally, sequentially driving pusher members 90, 90a, 90b to eject the fasteners 70 and the plugs 134, 134a from within staple cartridge 112. In particular, when the sled 80 engages pusher members 90, pusher members 90 drive fasteners 70 substantially vertically through fastener slots 116 by virtue of the distal driving force of the sled 80 into the pusher members 90 that cams the bottom surface of the pusher members 90 upwardly along an inclined surface of the sled 80. Likewise, when sled 80 engages pusher members 90a, 90b, pusher members 90a, 90b drive plugs 134, 134a substantially vertically through recesses 115, 115a by virtue of the distal driving force of the sled 80 into the pusher members 90a, 90b that cams the bottom surface of the pusher members 90a, 90b upwardly along an inclined surface of the sled 80.

Meanwhile, legs of the fasteners 70 penetrate through the tissue and the buttress body 132, 232 of the surgical buttresses 130, 230. The fasteners 70 are then formed against the fastener forming pockets 124 of the anvil plate 122 of the anvil assembly 120 thereby affixing the buttress body 132, 232 to the tissue. Concomitantly therewith, the knife 40 translatably disposed within the end effector 100, cuts through the tissue clamped between the cartridge assembly 110 and the anvil assembly 120 and through at least a portion of the buttress body 132, 232 by virtue of the leading edge 44 of the knife 40.

As the knife 40 translates along the knife channel 118, 126, a knife bar 42 of the knife 40 mechanically disrupts any plug 234, 234a positioned in the knife channel 126, as shown in FIG. 3B. In particular, the knife bar 42 is positioned proximally of the leading edge 44 of the knife 40 and substantially fills the width of a knife bar portion 126a of the knife channel 126. As the knife 40 distally translates, the knife bar 42 distally translates through the knife bar portion 126a of the knife channel 126 and pushes against the securement cap 238 of any plug 234, 234a positioned in knife bar portion 126a of the knife channel 126 to separate the securement cap 238 of the plug 234, 234a from the remainder of the respective plug 234, 234a. After the securement cap 238 of the plug 234, 234a has been separated from the remainder of the respective plug 234, 234a, the remainder of the plug 234, 234a may be pulled from the respective recess 128, 128a of the anvil assembly 120 by the formation forces applied to the surgical buttress 130, 230 by the fasteners 70 that are formed in the fastener forming pockets 124 of the anvil plate 122 of the anvil assembly 120 upon the firing of the surgical stapling apparatus 10.

Alternatively, the knife bar 42 of the knife 40 may act on the securement caps 238 of the plugs 234, 234a and press securement caps 238 of the plugs 234, 234a out of respective recesses 128, 128a to release surgical buttress 230.

In certain embodiments, the knife 40 can be configured and arranged to cut through the surgical buttresses 130, 230 prior to firing. Alternatively, the surgical buttresses 130, 230 can be cut with shears, or can include perforations or frangible features.

While the cartridge assembly 110 may be a single use loading unit, the user may remove the single use loading unit or portions thereof from the surgical stapling apparatus 10 and subsequently dispose the single use loading unit in its entirety or portions thereof. If further application is necessary, a user may replace the spent or fired single use loading unit by mounting a new single use loading unit, in the form of a new cartridge assembly and a new surgical buttress 130, 230 onto the surgical stapling apparatus 10. The user may then repeat a fastening process.

It is further contemplated that, if desired, an end user may remove surgical buttresses 130, 230 from cartridge assembly 110 or anvil assembly 120 prior to a use of surgical stapling apparatus 10.

In embodiments, the surgical buttresses 130, 230 are configured for use with surgical fastening devices for simultaneously applying an array of surgical fasteners, e.g., staples or other types of fasteners that are known in the art. Such devices are used for joining body tissue such as, for example, intestinal and gastric walls with spaced parallel rows of longitudinally aligned fasteners. These surgical fastening devices reduce the time of wound closure in a surgical procedure.

Typically, these devices include a fastener holder disposed on one side of the tissue to be joined, and an anvil assembly parallel to the fastener holder on the other side of the tissue to be fastened. The fastener holder is moved linearly towards the anvil assembly so that the tissue is clamped between them. The fasteners are driven from the fastener holder so that the ends of the fasteners pass through the tissue and form finished fasteners as they make contact with the anvil assembly, thereby producing an array of finished fasteners in the tissue. The fasteners can be one or two piece and made of metal, non-absorbable polymers, or bioabsorbable polymers such as plyglycolide, polylactide, and copolymers thereof.

U.S. Pat. No. 5,137,198 to Nobis et al. ("Nobis") discloses a fastener applying device including a cartridge that is advanced towards an anvil assembly by an advancing mechanism. The advancing mechanism includes a first actuator member for advancing the cartridge towards the anvil assembly at an accelerated rate and a second actuator member spaced from the first actuator member for incrementally advancing the cartridge towards the anvil assembly.

Typically, these fastener applying devices include a pusher bar that is advanced over a predetermined stroke to interact with and eject the fasteners from the cartridge. At least one driver is positioned within the cartridge between the distal end of the pusher bar and the fasteners such that the pusher bar advances the drivers into engagement with the fasteners. The length of the drivers may be varied to facilitate ejection of different size fasteners from a fastener applying device having a fixed pusher bar stroke. Such instruments are disclosed, for example, in U.S. Pat. No. 5,964,394, the entire content of which is incorporated herein by reference.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A method of mounting a surgical buttress to an end effector for a surgical stapling apparatus, the method comprising:
   providing an end effector for a surgical stapling apparatus, the end effector including a first jaw assembly defining a plurality of fastener retaining slots and a second jaw assembly defining a plurality of fastener forming pockets, at least one of the first and second jaw assemblies defining a plurality of recesses;
   providing a surgical buttress formed of a first material;
   providing a second material on the surgical buttress at predetermined locations on the surgical buttress;
   placing the surgical buttress against a tissue contacting surface of one of the first jaw assembly or the second jaw assembly;
   exposing the surgical buttress to heat and pressure to move the second material into the plurality of recesses; and
   removing the heat and pressure to interlock the second material within the plurality of recesses to secure the surgical buttress on at least one of the first jaw assembly or the second jaw assembly.

2. The method of claim 1, wherein the step of exposing the surgical buttress to heat and pressure results in a forming of the second material into a plurality of plugs integrally extending from the surgical buttress and that interlock within the plurality of recesses to secure the surgical buttress on at least one of the first jaw assembly or the second jaw assembly.

3. The method of claim 2, further including supporting a cartridge defining the retaining slots within the first jaw assembly and positioning the surgical buttress on a tissue contacting surface of the cartridge, wherein each of the plurality of plugs is configured and dimensioned to facilitate the release of the at least one surgical buttress from the cartridge upon a firing of the surgical stapling apparatus.

4. The method of claim 1, further including selecting the first material from a non-woven material.

5. The method of claim 1, further including selecting the second material from the group consisting of polyglytone 6211, glycolide, caprolactone, trimethylene carbonate, lactide and combinations thereof.

6. The method of claim 1, further including selecting the second material from a material having a melting temperature below a melting temperature of the first material.

7. The method of claim 6, wherein selecting the second material from a material having a melting temperature of between about 120 degrees Celsius and about 150 degrees Celsius, and further including selecting the first material from a material having a melting temperature of between about 180 degrees Celsius to about 225 degrees Celsius.

8. The method of claim 7, wherein exposing the surgical buttress to heat and pressure results in melting of the second material without melting of the first material.

9. A method of mounting a surgical buttress to an end effector for a surgical stapling apparatus comprising:
   placing a surgical buttress against at least one of a tissue contacting surface of a first jaw assembly or a second jaw assembly of an end effector for a surgical stapling apparatus, the first jaw assembly defining a plurality of fastener retaining slots and the second jaw assembly defining a plurality of fastener former pockets, at least one of the first or second jaw assemblies defining a plurality of recesses therein, wherein the surgical buttress is formed of a first material and includes a second material disposed at predetermined locations on thereon, wherein the second material of the surgical buttress overlies the plurality of recesses of the first or second jaw assembly;
   exposing the surgical buttress to heat and pressure to move the second material into the plurality of recesses; and
   removing the heat and pressure to interlock the second material within the plurality of recesses to secure the surgical buttress on at least one of the first jaw assembly or the second jaw assembly.

10. The method of claim 9, further including forming the first material from a non-woven material.

11. The method of claim 9, further including selecting the second material from the group consisting of polyglytone 6211, glycolide, caprolactone, trimethylene carbonate, lactide and combinations thereof.

12. The method of claim 9, further including selecting the second material from a material having a melting temperature below a melting temperature of the first material.

13. The method of claim 12, wherein selecting the second material from a material having a melting temperature of between about 120 degrees Celsius and about 150 degrees Celsius, and further including selecting the first material from a material having a melting temperature of between about 180 degrees Celsius to about 225 degrees Celsius.

14. The method of claim 13, wherein exposing the surgical buttress to heat and pressure results in melting of the second material without melting of the first material.

15. The method of claim 9, wherein exposing the surgical buttress to heat and pressure results in a forming of the second material into a plurality of plugs integrally extending from the surgical buttress and that interlock within the plurality of recesses to secure the surgical buttress on at least one of the first jaw assembly or the second jaw assembly.

16. The method of claim 15, further includes supporting a cartridge defining the retaining slots within the first jaw assembly and positioning the surgical buttress on a tissue contacting surface of the cartridge, wherein each of the plurality of plugs is configured and dimensioned to facilitate the release of the at least one surgical buttress from the cartridge upon a firing of the surgical stapling apparatus.

* * * * *